US012533482B2

(12) United States Patent
Kern

(10) Patent No.: US 12,533,482 B2
(45) Date of Patent: Jan. 27, 2026

(54) AEROSOLISED MEDICATION OF VENTILATED PATIENTS WITH MINIMISED DEAD VOLUME

(71) Applicant: STAMFORD DEVICES LIMITED, Dangan (IE)

(72) Inventor: Stefan Kern, Elsenfeld (DE)

(73) Assignee: STAMFORD DEVICES LIMITED, Galway (IE)

( * ) Notice: Subject to any disclaimer, the term of this patent is extended or adjusted under 35 U.S.C. 154(b) by 690 days.

(21) Appl. No.: 17/293,203

(22) PCT Filed: Dec. 6, 2018

(86) PCT No.: PCT/EP2018/083885
§ 371 (c)(1),
(2) Date: May 12, 2021

(87) PCT Pub. No.: WO2020/114603
PCT Pub. Date: Jun. 11, 2020

(65) Prior Publication Data
US 2022/0008672 A1 Jan. 13, 2022

(51) Int. Cl.
*A61M 16/08* (2006.01)
*A61M 16/04* (2006.01)

(52) U.S. Cl.
CPC .... *A61M 16/0833* (2014.02); *A61M 16/0463* (2013.01); *A61M 16/0477* (2014.02); *A61M 2240/00* (2013.01)

(58) Field of Classification Search
CPC .......... A61M 16/0833; A61M 16/0463; A61M 16/0477; A61M 16/00; A61M 2240/00;
(Continued)

(56) References Cited

U.S. PATENT DOCUMENTS

| | | | | | |
|---|---|---|---|---|---|
| 5,099,833 | A * | 3/1992 | Michaels | A61M 16/0833 128/200.14 |
| 5,357,946 | A * | 10/1994 | Kee | A61M 16/0825 128/200.23 |

(Continued)

FOREIGN PATENT DOCUMENTS

| | | | | |
|---|---|---|---|---|
| EP | 2 628 445 A1 | 8/2013 | |
| JP | 2003522003 A * | 7/2003 | A61M 15/0018 |
| WO | WO-2015025246 A2 * | 2/2015 | A61M 11/005 |

OTHER PUBLICATIONS

JP 2003522003 machine translation (Year: 2003).*
International Search Report mailed Jul. 5, 2019 in International Application No. PCT/EP2018/083885 (5 pages).

*Primary Examiner* — Victoria Murphy
*Assistant Examiner* — Sara K Toich
(74) *Attorney, Agent, or Firm* — Bookoff McAndrews, PLLC

(57) ABSTRACT

A coupling part with integrated aerosol generator for use in a breathing circuit, comprising a housing (10) enclosing a cavity (V), having a first opening at a first end prepared for direct or indirect connection to a ventilator, a second opening at a second end, which is suitable for direct or indirect connection to a patient line or an endotracheal tube, wherein an aerosol generator (20) is integrated in one side of the housing and is suitable for delivering an aerosolised liquid, in particular a medicament.

20 Claims, 2 Drawing Sheets

(58) Field of Classification Search
CPC . A61M 11/00; A61M 11/005; A61M 15/0085
See application file for complete search history.

(56) References Cited

U.S. PATENT DOCUMENTS

| | | | | |
|---|---|---|---|---|
| 2002/0020409 | A1* | 2/2002 | Kidwell | A61M 11/06 128/203.14 |
| 2004/0094150 | A1* | 5/2004 | Flynn | A61M 16/0057 128/202.28 |
| 2005/0139211 | A1* | 6/2005 | Alston | A61M 16/204 128/205.24 |
| 2007/0116649 | A1* | 5/2007 | Charan | A61J 1/065 514/35 |
| 2008/0000470 | A1* | 1/2008 | Minocchieri | A61M 16/0003 128/200.21 |
| 2009/0241948 | A1* | 10/2009 | Clancy | A61M 15/0085 128/203.14 |
| 2011/0011395 | A1* | 1/2011 | Mazela | A61M 16/0833 128/202.13 |
| 2011/0146670 | A1* | 6/2011 | Gallem | A61M 11/005 128/200.14 |
| 2012/0138049 | A1* | 6/2012 | Wachtel | A61M 16/0816 128/200.14 |
| 2013/0298904 | A1 | 11/2013 | Smaldone et al. | |
| 2014/0053831 | A1* | 2/2014 | Leamon | A61M 16/14 128/200.14 |
| 2014/0360498 | A1* | 12/2014 | Alizoti | A61M 11/00 128/203.12 |
| 2016/0263333 | A1* | 9/2016 | Dellaca | A61M 16/06 |

* cited by examiner

AEROSOLISED MEDICATION OF VENTILATED PATIENTS WITH MINIMISED DEAD VOLUME

CROSS-REFERENCE TO RELATED APPLICATION(s)

This patent application is the U.S. national phase entry under 35 U.S.C. § 371 of International Application No. International Application No. PCT/EP2018/083885, filed on Dec. 6, 2018, the entirety of which is incorporated herein by reference.

INTRODUCTION

The present invention relates to a coupling part for use in a breathing circuit with integrated aerosol generator comprising a housing enclosing a cavity, having a first opening at a first end, which is prepared for direct or indirect connection to a ventilator, a second opening at a second end, which is suitable for indirect or direct connection to a patient line or an endotracheal tube.

Breathing in humans and in all mammals is a cyclical process in which inhaled or inspired air is sucked in via the respiratory openings, the trachea, the lungs and from there via bronchi, bronchioles into the alveoli and after gas exchange in an exhalation process, the expiration, the air is ejected the same way in the opposite direction.

By using the respiratory tract once in one direction and once in the other direction for the passage of the respiratory gas during breathing, it follows that the air remaining in the respiratory tract is not renewed and so a certain amount of "spent" air is always inhaled during inhalation. "Spent" in this context means that the air has an increased $CO_2$ and reduced $O_2$ partial pressure in comparison to the ambient air.

The amount of air so inhaled is determined by the so-called dead volume. The physiological dead volume, which is naturally always present, is composed of the volume of the mouth and pharynx, the trachea and the bronchi. The latter are also included in the dead volume as there is no gas exchange in the bronchi. Only the air which actually reaches the alveoli during inhalation participates in the gas exchange, reducing the $O_2$ partial pressure of the inhaled air and increasing the $CO_2$ partial pressure. In contrast, the air in the physiological dead volume does not take part in the gas exchange in the inspiratory part of the respiratory cycle, but is heated to approximately body temperature and humidified. For the exhalation process, the opposite is true: the air remaining in the dead volume has a reduced $O_2$ content and an increased $CO_2$ content compared to the ambient air.

The dead volume makes up a significant proportion of the total respiratory volume, especially during tidal breathing. At rest, an adult person uses about half a litre of air per breath and has a physiological dead volume of about 150 ml, and so about one-third of spent air per tidal volume is inhaled (again). This proportion is reduced under load when a larger proportion of the maximum available lung capacity is used.

In the case of artificially ventilated persons, an additional dead volume is added to the physiological dead volume by the upstream breathing tube and any further devices connected thereto. It has long been known that care must be taken to keep this additional dead volume as low as possible because if the total dead volume, i.e. the sum of physiological dead volume and dead volume added by the breathing circuit, approaches the breathing volume per airflow, this means that with each breath ever greater proportions of spent air with reduced oxygen and increased carbon dioxide content enter the lungs. Accordingly, the oxygen supply to a person breathing in this way deteriorates. If the dead volume reaches or exceeds the tidal volume of the person, almost no fresh air enters the lungs, and in a first approach the same, spent air is always moved back and forth while breathing. The influx of $O_2$ or the removal of $CO_2$ only occurs by diffusion over the cross section of the opening to the ambient air. This is usually wholly inadequate for oxygen supply. Accordingly, the oxygen content will decrease to a value close to zero. A life-threatening hypoxia is the inevitable consequence.

It follows that in ventilated patients, who usually have only a relatively small tidal volume corresponding to the tidal breathing of a normal person or even less, care should be taken that the dead volume added by the breathing circuit remains as low as possible. This is true even for adult patients. Even more care should be taken in the artificial respiration of children and especially new-born or premature babies, because they have a much reduced tidal volume compared to adults. Although the physiological dead volume is also reduced to about the same extent, the use of breathing circuit components intended for adults is not possible in children or even new-borns, as these usually add a dead volume which is only a few orders of magnitude below the physiological dead volume of an adult.

Generally, the rule of thumb is that dead volumes added by the breathing circuit components should be only a fraction of the physiological dead volume and should not exceed it in any event. Accordingly, it can be seen that a dead volume of at most about five ml may be added in new-borns. This value is even lower for premature babies with correspondingly smaller lung capacity, the exact value depending on the specific birth week. In premature babies born before the $30^{th}$ week of pregnancy, a dead volume of at most one millilitre is usually acceptable.

An important measure to minimise the dead volume, which has been used since the beginning of artificial ventilation, is to divide the artificial breathing circuit into inhalation and exhalation branches. For this purpose, a usually Y-shaped coupling part is provided with three connections. A line leading to the patient is connected to one connection or an endotracheal tube is directly connected thereto. A line supplied by the ventilator with fresh air, the inspiratory line, is connected to the second connection. The third connection is reserved for the expiratory line, through which the spent air is sent back from the patient to the ventilator and, if necessary, filtered before being discharged into the ambient air.

Often, other medical therapeutic measures should also be performed in ventilated patients, such as the administration of medicaments or the suction of secretions from the bronchi or lungs. For this purpose it is necessary to connect further devices to the breathing circuit, for example a nebuliser for the aerosolization of a medicament fluid or a catheter for insertion into bronchi or trachea for aspirating mucus or other fluids accumulating therein.

The connection of additional medical devices, whether on the patient side or other parts of the breathing circuit, is usually effected by hollow cylindrical connections with plug-in or screw connections. These connecting pieces known from the prior art are simple to use, but they in part considerably increase the dead volume in the breathing circuit.

During breathing, the upper respiratory tract naturally has the function of warming and humidifying inhaled air so that air drawn into the lungs is approximately at body temperature and 100% air humidity. If artificial ventilation bypasses the natural airways, such as by inserting a tube into the trachea—either orally or through a tracheotomy—then this natural humectant function of the upper respiratory tract must be replaced. For this purpose, so-called HME filters are known which combine heat and humidity exchange with a filtration of microbes. In order to fulfil their function, these filters must be placed on the patient side of the division into the inspiratory and expiratory circuits. As with all devices mounted on the patient side, the dead volume also increases due to these HME filters.

Against this background, the object of the present invention is to provide a breathing circuit in which it is possible to administer medicaments in aerosolised form, and which can also be used to ventilate new-born and/or premature babies.

STATEMENTS OF INVENTION

As a solution, the present invention proposes a coupling part having the features of claim 1, which is used in particular as claimed in claim 10. The essential concept of the coupling part in accordance with the invention is to integrate the aerosol generator directly in one side of the housing, instead of connecting it, via a connecting piece or even indirectly via a hose leading to the connecting piece, as is usual in the prior art.

As a result of this integration of the aerosol generator in one side of the coupling part itself, the dead volume added to the breathing circuit is advantageously minimised. Theoretically, it can be completely eliminated, but in practice the fact remains that by integrating the aerosol generator a somewhat increased dead volume is unavoidable compared with a coupling part without an integrated aerosol generator. However, this construction-conditioned additional dead volume is limited to that volume which is required by the storage elements of the aerosol generator.

Aerosol generators which consist of a mesh membrane caused to vibrate by a piezoceramic are particularly suitable for such a use. Such mesh membranes are thin membranes, usually metal, which have a plurality of openings which have a cross-sectional tapering generally from an inlet side to an outlet side. On the one hand, such aerosol generators are extremely compact in themselves, and require only a minimum amount of bearing and sealing elements. In the case of the conventionally used round mesh membranes, which are caused to vibrate by an annular piezoceramic, indirectly or directly connected directly to the mesh membrane on the edges, these are a damping and sealing element, which is mounted on the opposite side to the piezoelectric and at that location ensures the sealing of the aerosol generator and the mechanical damping with respect to the housing. Such an aerosol generator can now be integrated into the side of the coupling part by providing an opening therein and creating a structure shaped complementarily to the holding and sealing elements of the aerosol generator, into which structure the aerosol generator is inserted.

The shape of the coupling part itself is of minor importance within the scope of the present invention. However, it is recommended, as is usual in the prior art, to provide a circular cross section for the air duct in the interior, as this minimises the surface area/volume ratio, which has positive consequences on the one hand for contamination and cleaning of the coupling part between the operating phases and on the other hand also for the maintenance of the humidity and temperature of the air flowing through the coupling part during operation.

However, the coupling part has in each case two openings, which are each assigned to one end. Each end is prepared for connection to other components of the treatment circuit. The first end of the connection-related coupling part is prepared for connection either directly to the ventilator, or to a branching part, at which the breathing circuit splits into the inspiratory and expiratory branches. In contrast, the second end with the second opening therein is suitable for connection to a line leading to the patient or directly to an endotracheal tube via a tracheotomy or orally inserted into the trachea of the patient.

The two ends, which are formed in an air duct with a circular cross section in an approximately hollow cylindrical shape, can form an angle which is ideally between 90° and 180°. An angle of 180° means that the coupling part is a straight continuous line piece. At an angle of 90°, there is an elbow piece, or in conjunction with the opening on the side to which the aerosol generator is connected or into which it is inserted, a T-piece.

The droplets of the aerosol generated by the aerosol generator on the outlet side have a certain average momentum. The direction of this average momentum is referred to as the outlet direction. This is the normal to the outlet side of the mesh membrane when using an ideal aerosol generator in the form of a nebuliser with a mesh membrane and piezoceramic.

Asymmetries in the piezo or ceramic may cause slight deviations from the normal direction. However, these are negligible in practice.

This preferred outlet direction now forms a certain angle with the flow, at the point at which the aerosol generator is integrated into the side of the coupling part, during the breathing, in particular inhalation process. This angle should not be greater than 90° and is preferably kept as small as possible. This can be achieved by positioning the second opening in the second end of the coupling part diametrically opposite the aerosol generator integrated in the side. As a result, it is achieved that the outlet direction described above extends directly out of the coupling part and into a tube or patient line connected thereto. This ensures the most complete possible entrainment of the generated aerosol by the air flow during inhalation.

Due to the advantageous avoidance of the connecting pieces, which are usual in the prior art, for connecting medical devices, such as nebulisers for administering aerosolised medicaments, a significantly smaller dead volume of the connecting piece according to the invention is achieved. The remaining dead volume is set, when using a mesh nebuliser, substantially by the sleeve or sealing ring, used to bear and seal the aerosol generator, on the outlet side of the mesh membrane, which usually has an approximately hollow-cylindrical or toroidal configuration. By integrating the aerosol generator into the coupling part in accordance with the invention, it is advantageously possible to reduce the additional dead volume to 1 millilitre or less. In this case, the coupling part in accordance with the invention is not more expensive than T-pieces usually known from the prior art plus an external nebuliser.

Advantageous developments of the present invention, which can be implemented individually or in combination, insofar as they are not mutually exclusive, will be described in more detail hereinafter.

The aerosol generator integrated into the sides of the coupling part in accordance with the invention is preferably a so-called mesh nebuliser which comprises a mesh membrane having a plurality of passage openings from an input side to an output side and a piezoceramic, the latter causing the mesh membrane to vibrate in the ultrasonic range, whereby medicament fluid accumulating on the input side is forced through the openings and is discharged on the output side as a fine-droplet aerosol. The average droplet size depends upon the hole size. This is usually set so that the droplets are deposited predominantly at the desired target location. If the medicament is to act in the bronchi, droplet sizes of more than 10 μm are preferred, if the deposition should take place predominantly in the bronchioles, the smaller branches of the bronchi, an average droplet size of 5-10 μm is ideal and, finally, if a medication of the alveoli is desired, droplet sizes of less than 5 μm are necessary. The distribution of droplet sizes usually follows a normal distribution with a standard deviation of about one to a few micrometres.

The construction-conditioned additional volume, which is produced by virtue of the fact that the aerosol nebuliser is integrated into the side of the coupling part, preferably corresponds to slightly less than 1/10 of the total cavity volume of the coupling part and is in particular less than 1 ml.

The cross section of the interior of the coupling part is substantially arbitrary within the scope of the invention. However, the cross section is preferably round, as this facilitates cleaning and minimises the condensation on the outer surfaces of the cavity and the heat dissipation over the outer surfaces. The first and the second openings are preferably round, corresponding to the round cavity. It follows that the first and second ends are formed as approximately hollow-cylindrical connectors, prepared or suitable for connection to other components of the breathing circuit.

It is particularly preferred that the aerosol generator outlet or the preferred outlet direction extends to the second opening, and in particular the aerosol generator is arranged diametrically opposite this opening. As a result, it is advantageously achieved that the aerosol droplets are introduced tangentially into the flow present during inhalation, and thus as little as possible aerosol is deposited on the walls of the coupling part, whereby it would be lost for the therapy of the patient.

In order to ensure that the coupling part in accordance with the invention, which has such a configuration, is correctly connected so that the patient line is connected to the second end and the ventilator to the first end, it is proposed to design the two ends differently. In particular, it is preferable to form the first end as a hollow cylinder having an outer diameter which corresponds to the clear width of the second end, which is likewise formed as a hollow cylinder. As a result, the coupling part in accordance with the invention can be used in a system of components which are formed as hollow-cylindrical connectors with two different outer diameters or clear widths. In order to facilitate positioning of the aerosol generator diametrically opposite the second opening, the angle between the first and second ends is preferably selected to be between 90° and 180°, and particularly preferably between 90° and 120°. Particularly preferably, the coupling part is formed as a rectangular T-piece, in which one arm forms the first end and the other arm forms the second end and the third arm is formed by aerosol generator integrated in the coupling part.

Further preferably, a medicament reservoir is provided on the input side of the aerosol generator which can be filled with medicament to be aerosolised.

Furthermore, the aerosol generator can have an interface, in particular a USB interface, for connection to a control unit.

Likewise, it is possible that the coupling part in accordance with the invention has connections in the form of connectors for other medical devices, wherein care should be taken here that the dead volume produced thereby remains minimal. This is e.g. achieved in that, if no medical device is connected to these connections, this is closed by a closure means which extends into the interior of the connector and completely fills same.

In accordance with the invention, the coupling part is used in particular for the artificial ventilation of patients with a particularly small lung volumes, in particular for new-born or premature babies. Ventilation means known from the prior art, which may also allow administration of an aerosolised medicament, are not suitable for this.

Further details, features and advantages of the present invention will become apparent from the exemplified embodiments explained in more detail hereinafter with reference to the figures. The embodiments are intended to illustrate the present invention and not to limit it in any way in its generality.

BRIEF DESCRIPTION OF THE DRAWINGS

The invention will be more clearly understood from the following description thereof given by way of example only with reference to the accompanying drawings in which:—

DETAILED DESCRIPTION

Figure 1:
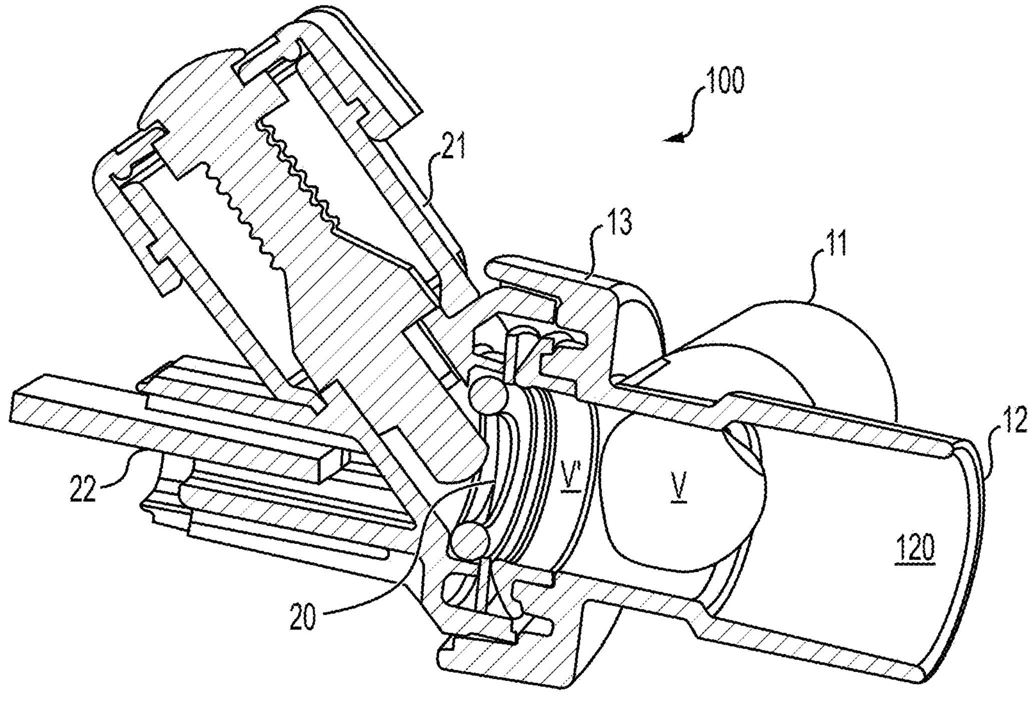
FIG. 1 shows a perspective longitudinal section through a preferred embodiment of the coupling part in accordance with the invention.

FIG. 1 shows a longitudinal section through a preferred embodiment of a coupling part in accordance with the invention. A coupling part 100 consists of a T-piece-shaped housing 10, with a first hollow-cylindrical end 11, a second hollow-cylindrical end 12 and a third end 13, the latter being formed as a partially double-walled hollow cylinder. The first and second ends each have a round opening 110, 120, through which breathing gas can flow into and through the inner space V enclosed by the housing 10. Connected to the inner hollow cylinder of the third end 13 and thus integrated in one side of the coupling part is an aerosol generator 20 in the form of a mesh nebuliser comprising a piezoceramic and thus a mechanically coupled membrane. Located on the input side of the aerosol generator is a medicament reservoir 21. The volume V' added to the inner space V owing to the construction due to the integration of the aerosol generator 20 is only about one tenth of the total volume V, which is slightly less than one millilitre. An interface 22 for connection to a control unit is likewise provided for the purpose of electrically actuating the piezoceramic.

Figure 2:
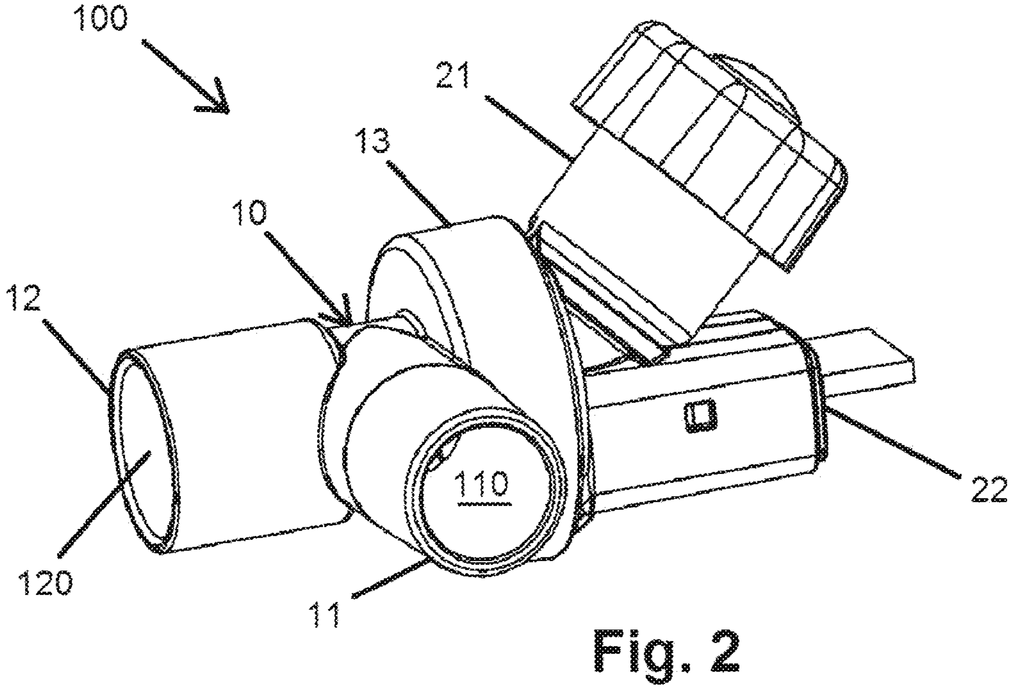
FIG. 2 shows a perspective external view of the coupling part from FIG. 1.

FIG. 2 shows the coupling part from FIG. 1 in a perspective view approximately from the direction of the first end 11. The first and second ends are substantially formed as hollow cylinders, wherein the first end 11 has an outer diameter which corresponds approximately to the inner diameter of the second end 12, and in any case differs in size from the second end 12. As a result, incorrect connection of the coupling part in accordance with the invention is effectively prevented. The first and second ends form, according to the T-shaped design, an angle of 90°. By virtue of the fact that the aerosol generator 20 is integrated in the third limb 13 of the T-piece, it is achieved that the outlet direction thereof, i.e. the average momentum vector of the generated aerosol droplets, which is ideally formed by the normal to the output side of the mesh membrane in the illustrated design, extends out of the second opening 120 and furthermore coincides with the axial direction of the hollow-cylindrical second end 12. This advantageously has the effect that the aerosol emerging from the aerosol generator is introduced tangentially into the air flow during the inhalation process and thus the losses of aerosol in the form of deposits on the inner walls of the coupling part in accordance with the invention are minimised.

Figure 3:
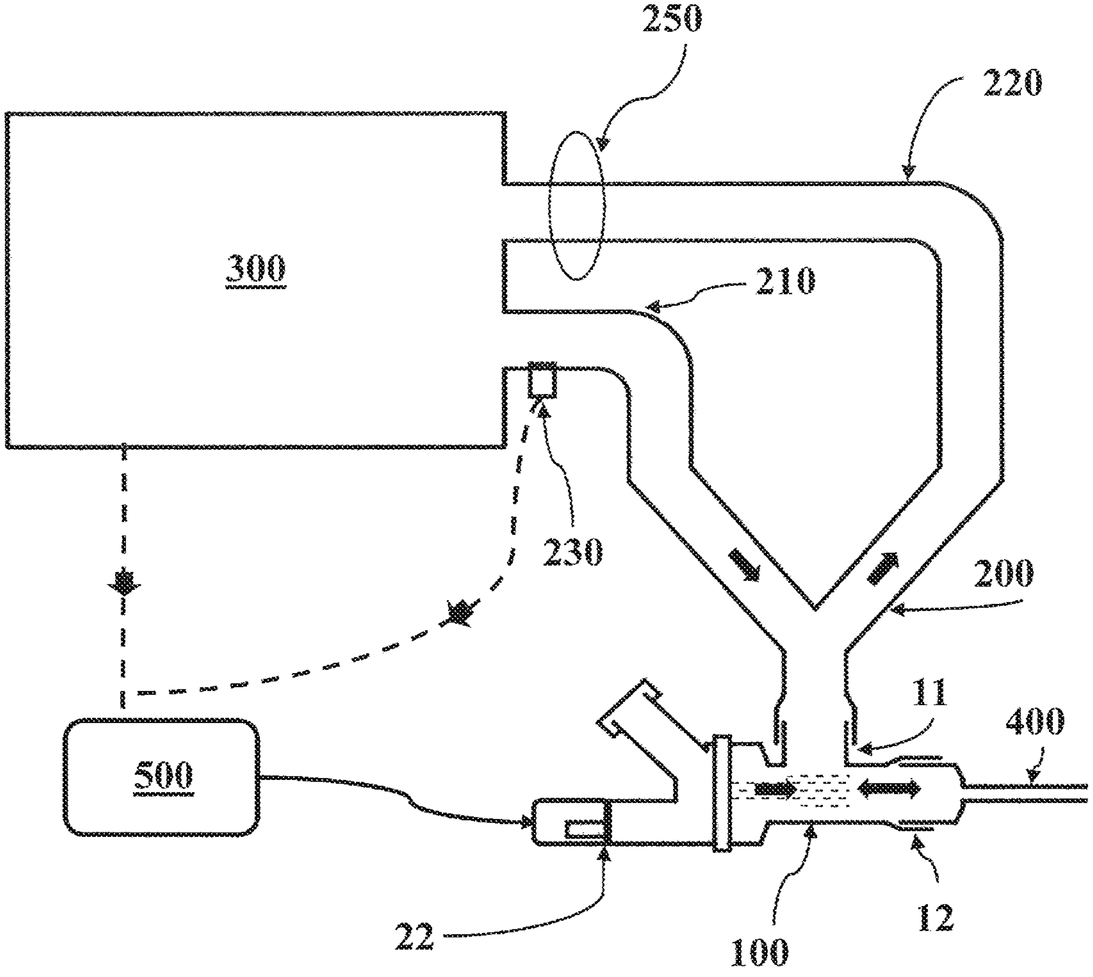
FIG. 3 shows a schematic structure of a breathing circuit using a coupling part in accordance with the invention.

FIG. 3 shows the schematic structure of a breathing circuit using the coupling part in accordance with the invention. The coupling part 100 is connected at its first end to a Y-piece 200, which in turn is connected with its two other limbs to the corresponding inputs and outputs of the ventilator 300 via an inspiratory branch 210 and expiratory branch 220 with a filter 250 respectively. The endotracheal tube 400 is placed onto the second end of the coupling part 100. A control unit 500 is connected via the interface 22 to the aerosol generator integrated in the coupling part 100. The aerosol delivery can be controlled either triggered by a pressure measurement by a sensor 230 in the inspiratory circuit, or else a time-variable output signal of the ventilator 300 is used to synchronise the aerosolization with the breathing.

LIST OF REFERENCE NUMERALS

10 Housing, T-piece
11 First end
12 Second end
13 Third end/limb
20 Aerosol generator
21 Medicament reservoir
22 Interface
110 First opening
120 Second opening
100 Coupling part
200 Y-piece
210 Inspiratory branch
220 Expiratory branch
230 Sensor
250 Filter
300 Ventilator
400 Tube
500 Control The invention is not limited to the embodiments hereinbefore described which may be varied in detail.

The invention claimed is:

1. A coupling part for use in a breathing circuit, comprising:
a housing enclosing a cavity and having:
a first arm forming a first hollow cylindrical channel defining a first opening configured for direct or indirect connection to a ventilator;
a second arm forming a second hollow cylindrical channel defining a second opening configured for direct or indirect connection to a patient line or an endotracheal tube,
wherein the second arm is perpendicular to the first arm, and
wherein the first hollow cylindrical channel coincides with the second hollow cylindrical channel to form an unobstructed air duct; and
a third arm formed by an aerosol generator integrated into the housing and configured to deliver an aerosolised liquid,
wherein the aerosol generator includes a mesh membrane,
wherein an outlet direction of the aerosolized liquid is normal to the mesh membrane and coincides with an axial direction of the second arm, and
wherein both the first arm and the second arm are downstream of the third arm along the outlet direction of the aerosolised liquid.

2. The coupling part as claimed in claim 1, wherein the aerosol generator comprises a piezoceramic.

3. The coupling part as claimed in claim 1, wherein the aerosol generator has a cross section which corresponds in shape and size to a cross section of the cavity.

4. The coupling part as claimed in claim 1, wherein the coupling part includes a total cavity volume, wherein a portion of the total cavity volume is a dead volume resulting from the integration of the aerosol generator, and wherein the dead volume is less than or equal to 1/10 of the total cavity volume.

5. The coupling part as claimed in claim 4, wherein the dead volume is less than or equal to 1 ml.

6. The coupling part as claimed in claim 1, wherein both a first internal end of the first hollow cylindrical channel open to the air duct and a second internal end of the second hollow cylindrical channel open to the air duct include a circular cross section.

7. The coupling part as claimed in claim 6, wherein a flow path from the first arm to the second arm is unimpeded.

8. The coupling part as claimed in claim 1, wherein the first arm and the second arm have different diameters.

9. The coupling part as claimed in claim 1, wherein the first and second arms form a T-shaped piece with the third arm formed by the aerosol generator.

10. The coupling part as claimed in claim 1, wherein there is provided a medicament reservoir.

11. The coupling part as claimed in claim 1, wherein the aerosol generator has an interface for connection to a control unit.

12. The coupling part as claimed in claim 11, wherein the interface is a USB interface.

13. The coupling part as claimed in claim 1, wherein the aerosol generator is positioned diametrically opposite the second opening.

14. The coupling part as claimed in claim 1, wherein the aerosolised liquid contains a medicament.

15. A coupling part with an integrated aerosol generator for use in a breathing circuit, comprising: a housing enclosing a cavity and comprising:
a first arm forming a first hollow cylindrical channel defining a first opening configured for connection to a ventilator; and
a second arm forming a second hollow cylindrical channel defining a second opening configured for connection to a patient line or an endotracheal tube,
wherein the first and second arms form an angle between 90° and 120° and
wherein the first hollow cylindrical channel coincides with the second hollow cylindrical channel; and
the aerosol generator integrated into the housing and configured to deliver an aerosolized liquid,
wherein an outlet direction of the aerosolized liquid coincides with the first hollow cylindrical channel and the second hollow cylindrical channel, and the axial direction of the second arm.

16. The breathing circuit as claimed in claim 15, wherein the first hollow cylindrical channel and the second hollow cylindrical channel coincide to form an unobstructed air duct.

17. The breathing circuit as claimed in claim 16, wherein the first arm and the second arm have different diameters.

18. The coupling part as claimed in claim 15, wherein the aerosolised liquid contains a medicament.

19. The coupling part as claimed in claim 15, wherein the aerosol generator comprises a piezoceramic.

20. A coupling part for use in a breathing circuit, comprising:

a housing enclosing a cavity;

an aerosol generator integrated into the housing and configured to deliver an aerosolised liquid;

a first arm integral to the housing, disposed downstream of the aerosol generator along an outlet direction of the aerosolised liquid, forming a first hollow cylindrical channel defining a first opening configured for direct or indirect connection to a ventilator; and a second arm integral to the housing, disposed downstream of the aerosol generator along the outlet direction of the aerosolised liquid, forming a second hollow cylindrical channel defining a second opening configured for direct or indirect connection to a patient line or an endotracheal tube, wherein the first hollow cylindrical channel coincides with the second hollow cylindrical channel such that a flow path from the first arm to the second arm is unimpeded.

* * * * *